United States Patent [19]
Ojo-Amaize et al.

[11] Patent Number: 5,994,328
[45] Date of Patent: Nov. 30, 1999

[54] HYPOESTOXIDES, DERIVATIVES AND AGONISTS THEREOF FOR USE AS ANTICANCER AGENTS

[75] Inventors: Emmanuel A. Ojo-Amaize, Glendora; Vellalore N. Kakkanaiah, Los Angeles, both of Calif.; Joseph I. Okogun, New Rochelle, N.Y.

[73] Assignee: Immune Modulation, Inc., Bloomington, Calif.

[21] Appl. No.: 09/006,946

[22] Filed: Jan. 14, 1998

[51] Int. Cl.[6] .................. A61K 31/665; A61K 31/535; A61K 31/335
[52] U.S. Cl. .................. 514/100; 514/232.8; 514/475
[58] Field of Search .................. 514/100, 475, 514/232.8

[56] References Cited

U.S. PATENT DOCUMENTS 5,801,193  9/1998  Ojo-Amaixe et al. .................. 514/475

Primary Examiner—Jerome D. Goldberg
Attorney, Agent, or Firm—Pillsbury Madison & Sutro LLP

[57] ABSTRACT

A method for inhibiting the growth of cancer cells ous tumors. The method comprises administering to a subject in need of anticancer or antitumor therapy a pharmaceutical composition comprising a therapeutically effective amount of a compound of the formula

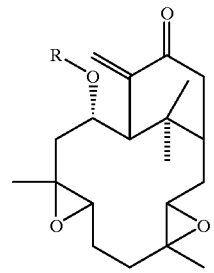

I where:
R is
(i) H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_nCOOR_2$ where n=1–4 where $R_2$ is H, an alkali metal salt, an alkaline earth metal salt, $NH_4^+$, $N^+(R_3)_4$ where $R_3$ is independently selected from the group consisting of H and alkyl of 1 to 4 carbon atoms, or
(ii) $COR_1$ wherein $R_1$ is selected from the group consisting of H, $(CH_2)_nCH_3$, where n=0–6, $(CH_2)_nCOOR_2$ where n=1–4 and $R_2$ is previously defined, $(CH_2)_nN^+(R_3)_4$ wherein n=1–4, and $(CH_2)_nSO_3^-$ where n=1–4, and pharmaceutically acceptable salts thereof.

3 Claims, 6 Drawing Sheets

HYPOESTOXIDES, DERIVATIVES AND AGONISTS THEREOF FOR USE AS ANTICANCER AGENTS

BACKGROUND OF THE INVENTION

1. Field of the Invention

This invention relates to the use of diterpene compounds, in particular hypoestoxides, derivatives and agonists thereof for inhibiting tumor growth.

2. Background Art

The strongest impetus for the many decades of research in tumor biology has been the hope that effective therapeutic agents might be found cytotoxic against tumor cells that could be used for prevention and therapy of cancer.

Malignant melanoma continues to increase in incidence. Currently, malignant melanoma is the fifth most frequently occurring cancer in the U.S. While early melanoma is highly curable by surgical means, the prognosis of patients with more advanced lesions and/or metastatic disease remains poor (Bezwoda, W R; Cancer Treat Rev 1997;23(1):17–34). Conventional chemotherapy with single-agent activity has a low frequency and short duration of response (Cancer Treat Rev 1997; 23(1):17–34); Mayo Clin Proc 1997;72:367–371).

Metastatic renal cell carcinoma (RCC) is highly resistant to the many systemic therapies that have been extensively investigated (Motzer R J et al. Current Problems in Cancer, 1997;21(4):185–232). RCC occurs nearly twice as often in men as in women. Increased availability of improved and highly sophisticated diagnostic methods such as ultrasonography and computed tomography (CT) scanning (Franklin J R et al. Seminars in Urologic Oncology 1996;14(2):208–215) has revealed a steadily rising incidence of RCC. Cervical carcinoma is the most common malignancy among women in developing countries (Morrow C P et al. J Cell Biochem 1995; suppl 23:61–70) and the third most common malignancy of the female genital tract in the Unites States (Miller B A et al. National Cancer Institute; NIH publication 93–2789, 1993).

All of the subsequent technological advances, including high dose rate therapy, treatment planning, new isotopes, new imaging techniques, and new machines, have had no clinically measurable effect on the curability of cervical cancer (Morrow C P et al. J Cell Biochem 1995; suppl 23:61–70).

Because neurotoxicity and chemotherapeutic drug resistance remain some of the major clinical problems associated with failure in the therapy of human cancer (Anticancer Drugs 1995;6(3):369–383; Curr Opin Oncol 1997;9(1):79–87), there is a need for study of new agents with fewer side effects and maximum efficacy.

DISCLOSURE OF THE INVENTION

Applicants' invention rests on their finding that a select group of hypoestoxide analogs possess unexpected effectiveness as anticancer agents. In particular, the present invention comprises a method for inhibiting the growth of cancer cells or cancerous tumors. The method comprises administering to a subject in need of anticancer or anticancer therapy a pharmaceutical composition comprising a therapeutically effective amount of a compound of the formula

I where:
R is
(i) H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_nCOOR_2$ where n=1–4 where $R_2$ is H, an alkali metal salt, an alkaline earth metal salt, $NH_4^+$, $N^+(R_3)_4$ where $R_3$ is independently selected from the group consisting of H and alkyl of 1 to 4 carbon atoms, or
(ii) $COR_1$ wherein $R_1$ is selected from the group consisting of H, $(CH_2)_nCH_3$, where n=0–6, $(CH_2)_nCOOR_2$ where n=1–4 and $R_2$ is previously defined, $(CH_2)_nN^+(R_3)_4$ wherein n=1–4, and $(CH_2)_nSO_3^-$ where n=1–4, and pharmaceutically acceptable salts thereof.

One aspect of the method involves administration of a hypoestoxide (herein designated JO-4A) having the formula:

II

MODES OF CARRYING OUT THE INVENTION

General Description and Definitions

The practice of the present invention will employ, unless otherwise indicated, conventional molecular and cell biology, cell culture, biochemistry, and organic and medicinal chemical synthesis within the skill of the art. Such techniques are explained fully in the literature. See *Cancer Chemotherapy: Principles and Practice,* ed. B. A. Chabner, J. M. Collins, Phil., Lippincott Publ., 1990; *Mechanisms of Interferon Actions,* Vol. II, ed. L. M. Pfeffer, CRC Press, Boca Raton, Fla. 1987; *Interferons: Principles and Medical Applications,* ed. S. Baron, D. Coppenhauer, F. Dianzani, et al., The University of Texas Medical Branch, Galveston, 1992; Robins, R. K., Ojo-Amaize, E. A., Cottam, H. B., et al., Nucleoside and nucleotide modulation of genetic expression: A new approach to chemotherapy. In: *Advances in Enzyme Regulation,* 1989, Vol. 29, *Cancer: Principles and Practice of Oncology;* ed. de Vita, Jr., V. T., Hellman, S., and Rosenberg, S. A., Lippincott Co., Philadelphia, 1993; *The Chemotherapy Source Book,* ed. Perry, M. C., Williams and Wilkins Publ., Baltimore, 1991). Silverman, Richard B., The Organic Chemistry of Drug Design and Drug Action, Academic Press, Inc. NY (1992); Smith, Michael B., Organic Synthesis, McGraw Hill, Inc., NY, (1994)).

The following terminology will be used in accordance with the definitions set out below in describing the present invention.

Although "tumor" simply means "swelling", the term is usually equated with "neoplasm", which literally means "new growth". A neoplasm is an abnormal mass of tissue that persists and proliferates after withdrawal of the carcinogen that initiated its appearance. There are two types of neoplasms or tumors, benign and malignant. The common term for all malignant tumors is "cancer". Nearly all benign tumors are encapsulated. In contrast, cancerous tumors are almost never encapsulated but invade adjacent tissue by infiltrative destructive growth. Invasive growth may be followed by tumor cells implanting at sites discontinuous with the original tumor usually through lymphatic and/or hematogenous spread of the cancer cells. This process, called "metastasis," unequivocally marks a tumor as malignant because a benign tumor never metastasizes whereas most cancers can metastasize (In: Pathologic basis of disease, 4th ed. Philadelphia: W B Saunders, 1989;239–305). It will be understood that the present method for inhibiting the growth of cancer cells or canceorous tumors includes inhibiting invasive growth of cancer cells as well as inhibiting metastatic growth of tumors from metastisized cancer cells.

The term "subject" is taken to mean humans as well as other animals.

As used herein, the term "JO-4" means a compound which is a bicycle [9,3,1] pentadecane diterpene compound, as described in Z. Naturforsc 37c: 558–561 (1982) and in Heterocycles 20:2125–2128 (1983), in which reference this compound is named "hypoestoxide." The chemical structure of JO-4 is illustrated in formula III.

III

It is understood that the compounds illustrated in formula I include prodrugs of JO-4A. In terms of formula I, JO-4A is derived from JO-4 when R is H. The structure of JO-4A is illustrated in formula II.

II

The term "prodrug," as used herein, refers to a pharmacologically inactive compound that is converted to an active drug by a metabolic transformation. (Silverman, Richard B. The Organic Chemistry of Drug Design, Acad. Press, 1992). There are numerous reasons why a prodrug strategy is used in drug design, the most common of which are to overcome problems associated with the compound, such as solubility, absorption and distribution, site specificity, instability, prolonged release, toxicity, poor patient acceptability, and formulation. Literature is available for guidance without undue experimentation for determining how to get compounds in pharmaceutical compositions to a locus to permit them to act, and guidance for how to obtain a therapeutically effective amount for inhibiting the growth of cancerous tumors at the locus of action (Brunda, M. J., Wright, R. B., Luistro, L. et al., Enhanced Antitumor Efficacy in Mice by Combination Treatment with Interleukin-1α and Interferon-α, *J.*

Immunother., (1994) 15:233–241; Bezwoda, W. R., The Treatment of Disseminated Melanoma with Special Reference to the Role of Interferons, Vinca Alkaloids, and Tamoxifen, *Cancer Treatment Review,* (1997) 23:17–34; Wedge, S. R., Porteous, J. K., Newlands, E. S., Effect of Single and Multiple Administration of an $O^6$-benzylguanine/temozolomide Combination: An evaluation in a Human Melanoma Xenograft Model, *Cancer Chemother. Pharmaocol.* (1997) 40:266–272).

The most common prodrug form for drugs containing alcohol or carboxylic acid functional groups is an ester. Using skills well known in the art, it is possible to alter the structure of the compound to improve its pharmacokinetic properties and, thereby, transform it into a useful drug for therapeutic administration to an animal or human. JO-4 is a prodrug for JO-4A in the presence of serum esterases in the in vivo setting, and, in the in vitro setting if the culture medium contains added serum (which is most often the case). A preferred embodiment of the hypoestoxide compound for use in the method for inhibiting the growth of cancerous tumors is the metabolite JO-4A, which is the free alcohol derivative of JO-4. JO-4 serves as an ester prodrug form for the delivery of JO-4A, which is formed over time after administration of JO-4 to cells or animals. In similar fashion, many other ester prodrugs of JO-4A provide delivery of JO-4A. Such prodrug forms and methods for making them are well known in the art, as cited above. These prodrugs are known to yield the parent drugs of interest upon exposure to esterases commonly found in serum of animals and humans. It is understood that the prodrugs of JO-4A useful in the claimed method yield JO-4A and are active in terms of inhibiting the growth of cancerous tumors.

The term "agonists" as used herein refers to substances that elicit the same response (i.e. inhibiting the growth of cancerous tumors in subjects in need of such treatment) as the compounds indicated in formula I. Agonists of the compounds of formula I include, but are not restricted to the prodrugs of JO-4A, which prodrugs are illustrated in formula I.

Methods for determining or screening modified forms of the hypoestoxide compounds i.e. prodrugs and/or agonists of the claimed compounds, for their ability to inhibit the growth of cancerous tumors in subjects in need of such treatment are well known in the art (Stinson, S., Alley, M. C., Kopp, W. C. et al. , Morphological and Immunocytochemical Characteristics of Human Tumor Cell Lines for Use in a Disease-Oriented Anticancer Drug Screen, *Anticancer Research* (1992) 12:1035–1054).

The method of the present invention is directed to anticancer or antitumor therapy, i.e. inhibiting the growth of cancer cells, and thereby, when the growth of cancer cells results in the develoment of one or more tumors, inhibiting the growth of cancerous tumors using the compounds of formula I, and in particular, the compounds of formula II (JO-4A, i.e. hypoestoxide). In particular, the method of the present invention involve administering to a subject in need of such treatment a therapeutically effective amount of at least one hypoestoxide compound of formulas I, and in particular the compound of formula II (JO-4A). An embodiment of the method involves associating compounds of formulas I or, in particular, II with a pharmaceutical carrier or diluent for administration to an subject.

Figure 1A:
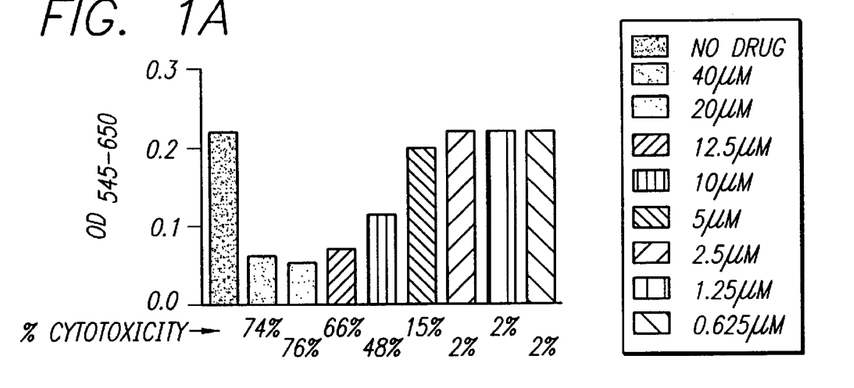
FIG. 1 shows the dose-dependent cytotoxic effects of JO-4A on various human cancer cells. Human cervical epitheloid carcinoma, renal carcinoma and malignant melanoma cell lines were cultured for 72 hours either in the presence or absence of various concentrations of JO-4A. Cytotoxicity was determined by calorimetric (MTT) assay.
Figure 1B:
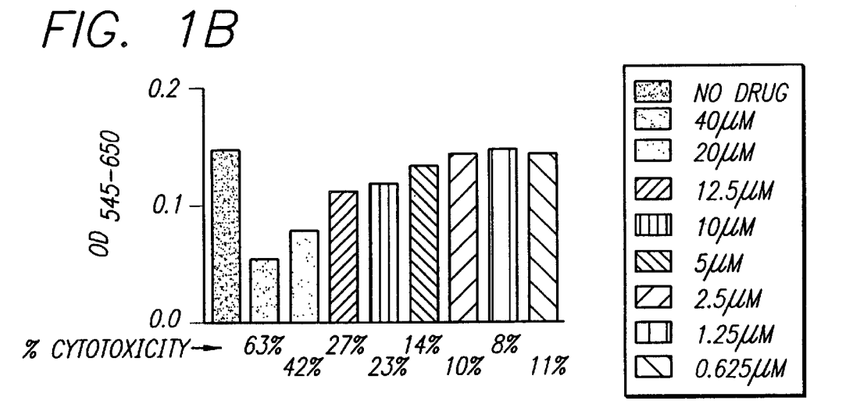
Figure 1C:
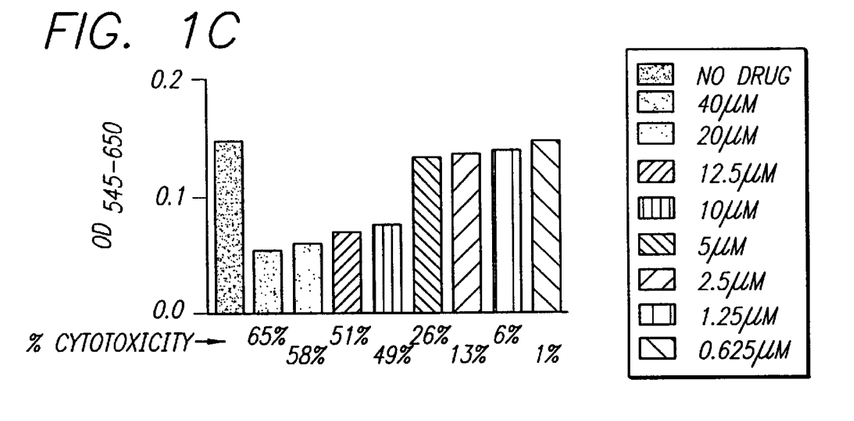
Figure 2A:
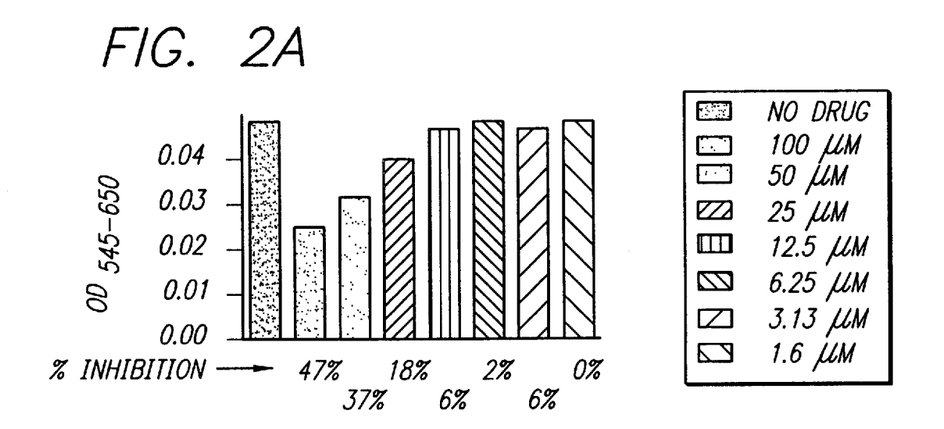
FIG. 2 shows the dose-dependent cytotoxic effects of JO-4A on normal human cells of various tissue origin. Normal human cervical ectoepithelial cells, peripheral blood mononuclear cells, mammary epithelial cells and umbilical vein endothelial cells were cultured either in the presence or absence of various concentrations of JO-4A for 72 hours. Cytotoxicity was determined by calorimetric (MTT) assay.
Figure 2B:
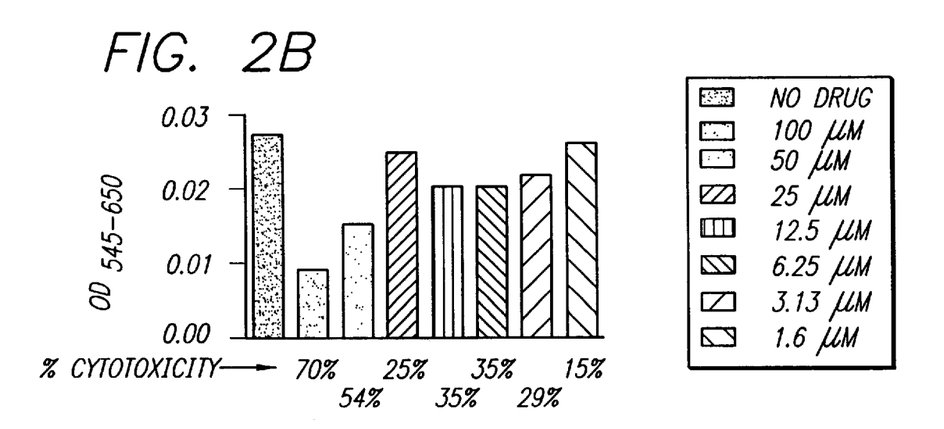
Figure 2C:
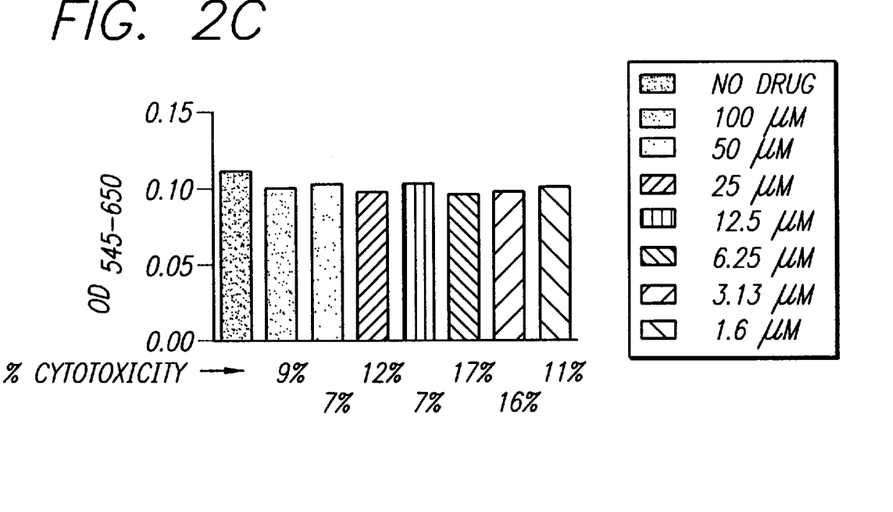
Figure 2D:
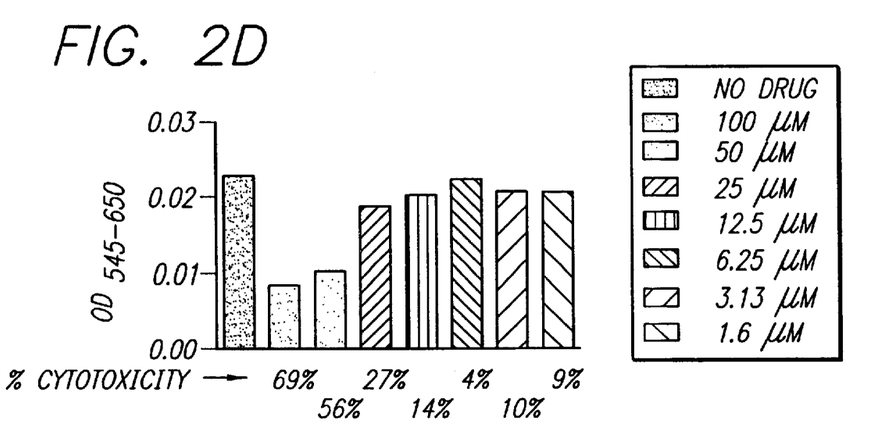
Figure 4A:
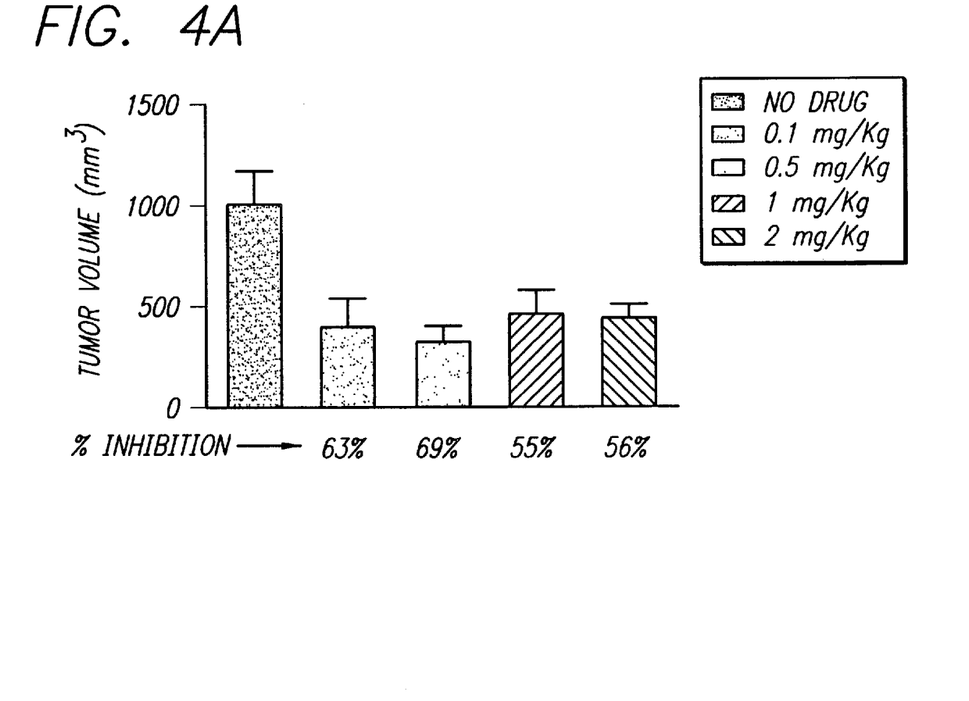
FIG. 4A shows the effect of oral administration of JO-4A on mouse malignant melanoma (B16-F1) volume in C57BL/6 (B6) mice. B6 mice received 50,000 B16-F1 viable cells subcutaneously (s.c.). Mice in the experimental groups received different concentrations of JO-4A orally everyday starting from day 4 after tumor implantation. Tumor volume was measured on day 12 using a microcaliper.
Figure 4B:
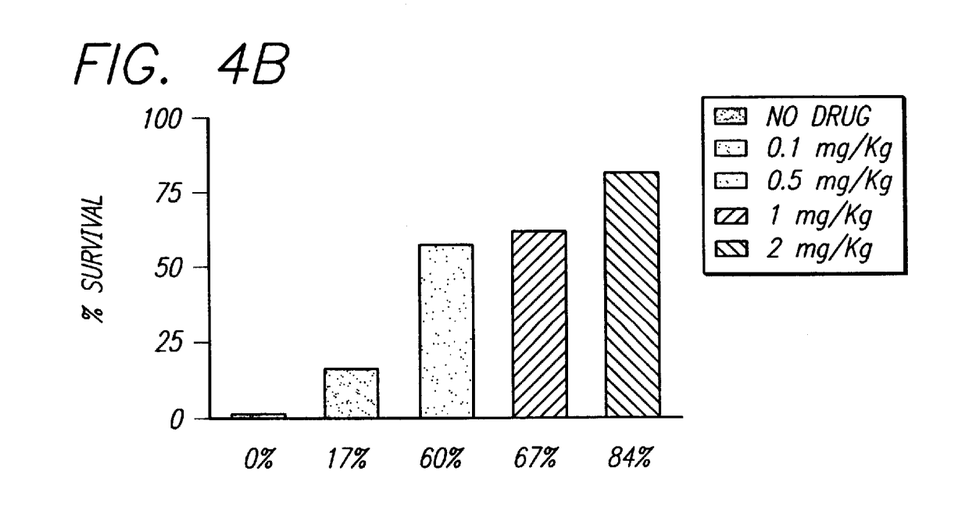
FIG. 4B shows the effect of oral administration of JO-4A on the survival of malignant melanoma (B16-F1) bearing B6 mice. B6 mice received 50,000 B 16-F1 viable cells subcutaneously (s.c.). Mice in the experimental groups received different concentrations of JO-4A orally everyday from day 4 post tumor implantation to day 20. Percent survival of mice in the experimental groups was calculated when all the mice in the non-treated control group were dead (day 28).
Figure 5:
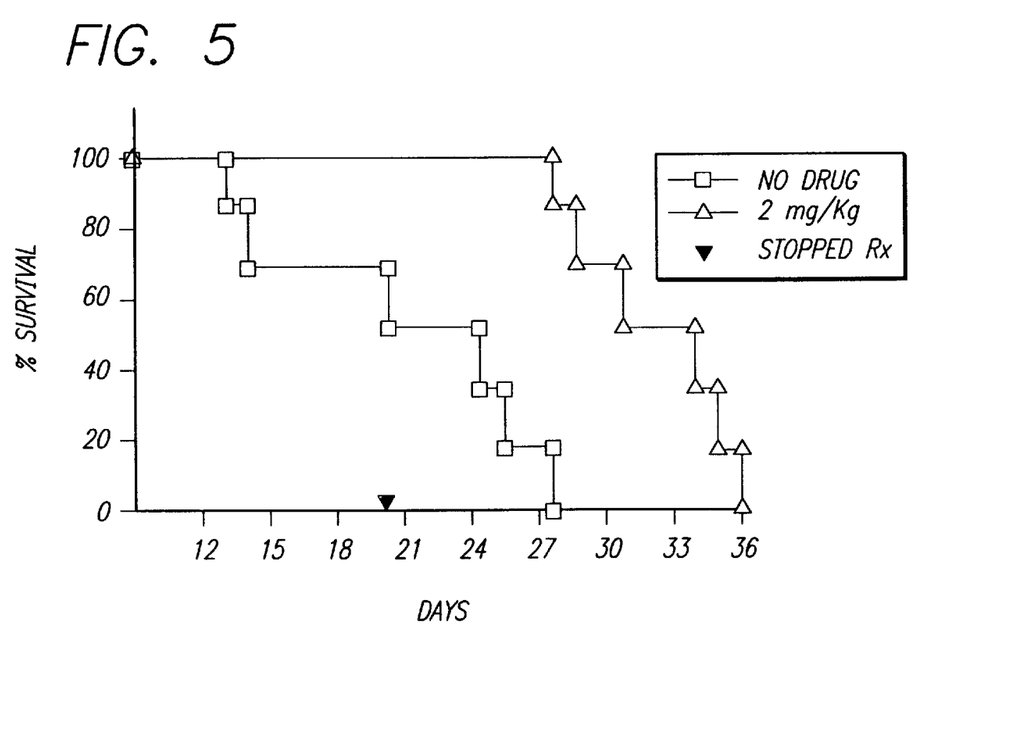
FIG. 5 shows the effect of oral administration of JO-4A on the survival of B 16-F1 melanoma bearing B6 mice. B6 mice received 50,000 B16-F1 viable cells subcutaneously (s.c.). Mice in the experimental group received JO-4A (2 mg/Kg) orally everyday from day 4 to day 20.

The method of the invention finds use in inhibiting the growth of cancerous cells in vitro, as illustrated in FIGS. 1, and in inhibiting the growth of cancer cells or cancerous tumors in mice, as shown in FIGS. 4 and 5. Thus, the method of the invention finds use in having a cytotoxic, growth-inhibiting effect on cancerous cells or cancerous tumors, and, at the same dosage level, having a relatively non-toxic effect on normal cells (FIG. 2), which differential toxic effect appears to inhibit the growth of cancerous tumors, and is therefore useful in anti-tumor treatment at least for the variety of cancer types indicated in FIG. 1. The effects of JO-4A were ascertained in the tests described below, as illustrated in FIGS. 1–6, showing that the method of the invention is effective for treating subjects in need of anti-cancer therapy.

For the above-mentioned use, the therapeutic effective amount or dosage will, of course, vary depending on the compound employed, mode of administration and treatment desired. However, in general, satisfactory results would be obtained when administered orally at a daily dosage of from about 0.01 mg to about 1000 mg per kg animal body weight, conveniently given in divided doses 1 to 4 times a day or in sustained release form. If administered by intravenous injection, in general, satisfactory results would be obtained when administered at a daily dosage of from about 0.01 mg to about 200 mg per kg animal body weight, conveniently given in divided doses 1 to 4 times a day or in sustained release form. For the larger mammals, the total daily dosage would be in the range of from about 1 to about 1000 mg, and dosage forms suitable for oral administration comprise from about 1 mg to about 1000 mg of the compound admixed or in association with a solid or liquid pharmaceutical carrier or diluent. Methods are well known in the art for determining therapeutically effective amounts of the compounds used in the method of the invention. Such methods involve analysis of the pharmaceutical/pharmacokinetic parameters in anti-cancer or antitumor therapy, i.e for inhibiting the growth of cancerous tumors (Wedge. S. R., Porteus, J. K., Newlands, E. S., *Cancer Chemother. Pharmacol.* (1997)40:266–272 Legha, S. S., *Seminar in Oncology,* (1997)24:S4-24-31; Motzer, R. J., Vogelzang, N. J., Chemotherapy for Renal Cell Carcinoma. In: Raghaven, D., Scher, H. I., Leibel, S. A., et al: eds. *Principles and Practice of Genitourinary Oncology,* Lippincott-Raven Publ., Philadelphia, pp. 885–96, 1997; Bloom, H. J., Medroxyprogesterone acetate (Provera) in the treatment of metastatic renal cancer, *Br. J. Cancer* (1971)25:250–65)

The method of the present invention includes administering a pharmaceutical composition comprising an effective amount of one or more of the compounds of formula I, and in particular the compound of formula II (JO-4A) in pure form or as a pharmaceutically acceptable crude concentrate in association with a pharmaceutical carrier or diluent. Such compositions conveniently contain less than 1% by weight, and preferably about 0.2% by weight, of the compounds of formulas I or, in particular, II, and may be prepared by conventional powders, syrups, elixirs, suspensions or solutions for enteral or parenteral administration. Suitable pharmaceutical diluents or carriers include, for example, water, alcohols, natural or hardened oils and waxes, calcium and sodium carbonates, calcium phosphate, kaolin, talc and lactose as well as suitable preserving agents, such as ethyl-p-hydroxybenzoate, suspending agents such as methyl cellulose, tragacanth and sodium alginate, wetting agents such as lecithin, polyoxyethylene stearate and polyoxyethylene sorbitan mono-oleate, granulating and disintegrating agents such as starch and alginic acid, binding agents such as starch, gelatin and acacia and lubricating agents such as magnesium stearate, stearic acid and talc, in order to provide an elegant and palatable pharmaceutical preparation. Compositions in tablet form may be coated by conventional techniques to delay disintegration of the tablet and absorption of the active ingredient in the gastrointestinal tract and thereby provide sustained action over a long period. Other compounds and methods known in the art for delaying disintegration or for timed-delayed or time-measured delivery of the active ingredients also find use in formulating the active ingredients for use in the methods of the invention. For example, the compounds of formulas I or in particular II may also be combined with liposomes or other delayed-release carrier means to protect the compounds from degradation until they reach their targets and/or facilitate movement of the compounds across tissue barriers.

The preferred compositions from the standpoint of ease of administration are solid compositions, particularly solid-filled gelatin capsules or tablets.

It is also to be understood that a further embodiment of the method of the invention involves combining one or more agents in a variety of protocols, including prophylaxis, with the method of the invention for administering to subjects in need of treatment for inhibiting the growth of cancerous tumors pharmaceutical compositions comprising compounds of formulas I or, in particular, II. Combination protocols and methods for determining their efficacy, including therapeutic drug monitoring, are well known in the art. Examples of anti-cancer agents and other agents useful in therapy for inhibiting the growth of cancerous tumors which may be combined with administering the compounds of formulas I or in particular II in the method of the invention include, but are not limited to radiation, interferon-$\alpha$, interleukin-1, -2, vinca alkaloids, tamoxifen, taxol, decarbazine, biological response modifiers, platinum compounds, vinvlatine, bleomycin, dexverapaimil, nifedioine, dipyridamole, carmustine, cisplatin.

It will be further understood that the present invention includes a method for inhibiting the growth of cancerous tumors which comprises administering to a subject in need of anticancer treatment pharmaceutical composition comprising a therapeutically effective amount of one or more compounds of formulas I and/or II (JO-4A) in association with one or more agents selected from the group of anti-cancer agents or agents useful in inhibiting or preventing growth of cancerous tumors consisting of radiation, interferon-$\alpha$, interleukin-1, -2, vinca alkaloids, tamoxifen, taxol, decarbazine, biological response modifiers, platinum compounds, vinvlatine, bleomycin, dexverapaimil, nifedioine, dipyridamole, carmustine, cisplatin. Methods are well known in the art for determining therapeutically effective amounts of the compounds of formulas I or II and agents selected from the group of anti-cancer agents or agents useful in anti-cancer therapy in association with the compounds of formulas I or II in pharmaceutical compositions in the method of the invention (William, S. D., ed., *Current Problems in Cancer,* Vol. 21, No. 4, 1997; pp. 186–221; Bezwoda, W. R., *Cancer Treatment Reviews,* 1997, Vol. 23:17–34)

The following materials and methods were employed in the non-limiting Examples set out below.

Tumor Cells

Human cervical epitlheloid carcinoma (HeLa), human renal clear cell carcinoma (CAKI-1), human malignant melanoma (RPMI-795 1) and mouse malignant melanoma (B 16-F1) were procured from ATTC (Rockville, Md.) and maintained in vitro with MEM medium (Mediatech, Inc., Herndon, Va.) supplemented with 10% heat-inactivated fetal bovine serum (American Qualex, San Clemente, Calif.), 10 mM glutamine, 100 U/ml penicillin, and 100 $\mu$g/ml streptomycin (Sigma Chemicals, Saint Louis, Mo.) (complete medium).

Normal Cells

Normal human cervical ectoepithelial cells (CrEc-Ec), normal human mammary epithelial cells (HMEC) and normal human umbilical vein endothelial cells (HUVEC) were obtained from Clonetics (San Diego, Calif.) and cultured with the respective recommended tissue culture medium obtained from Clonetics.

Peripheral Blood Mononuclear Cells (PBMC)

Heparinized venous blood was obtained from healthy adult volunteers and PBMC were separated by centrifugation over Ficoll-Hypaque (Pharmacia Biotech, Piscataway, N.J.). The cells were washed three times with HBSS (Hanks Balanced Salt Solution) and finally resuspended in complete medium. Cell viability was assessed by trypan blue dye exclusion test and the cell number was adjusted to required concentration.

Colorimetric MTT Assay

Cytotoxic effects of the hypoestoxide compounds of formulas I and II (JO-4A) were determined in vitro by a calorimetric assay (Mosmann, T., J. *Immunol. Methods,* 65:55–63, 1983). Briefly, 1000 cells per well (100 $\mu$l) in a 96-well flat-bottom plate were cultured either with the culture medium alone or with various concentrations of drug at 37° C., in a 5% $CO_2$-95% air humidified incubator for 72 hours. At the end of the culture, 10 $\mu$l of 5 mg/ml sterile solution of 3-(4,5-Dimethylthiazol-2yl)-2,5-diphenyltetrazolium bromide (MTT) (Sigma Chemicals, Saint Louis, Mo.) in PBS was added per well and the incubation was resumed for an additional 4 hours. Acid-isopropanol (100 $\mu$l of 0.04 N HCl in isopropanol) was added to all wells and kept at room temperature for 30 minutes. Mixing with a multichannel pipetter dissolved the dark blue crystals and the absorbance was measured at 545–650 nm using an ELISA plate reader.

Mice

Eight-week-old female C57BL/6 (B6) mice were purchased from Charles River Laboratories (Wilmington, Mass.

The Measurement of Tumor Volume in Mice

B16-F1 melanoma cells growing exponentially in vitro were harvested by 15 minutes incubation with 0.25% trypsin-EDTA solution (Irvin Scientific, Irvine, Calif.). The mice were given subcutaneous (s.c.) injections of 50,000 viable cells on the right side (Fidler, I. J. *Cancer Research* 35:218–224, 1975). Four days after injection, the mice in the experimental group were gavaged orally with various concentrations of JO-4A in 0.2 ml of water and the control group received water alone. The tumors were measured with a microcaliper, and the tumor volume was calculated by the formula: Length×width×height×0.5236 (Jungwirth, A. et al., *Proc. Natl. Acad. Sci. USA,* 94:5810–5813. 1997).

Statistical Analysis

Student's t-test was used to calculate the level of significance.

Compounds Used in the Method

The compounds tested in the method of the invention included JO-4A (formula II), JO-4 (formula I), which is an ester of JO-4A, and JO-4B (formula IV).

Compound Preparation

Preparation of JO-4A

JO-4 crystals (82 mg, 0.22mmol) were dissolved in a mixture of methanol (3 mL) and dioxane (3 mL) with warming and then cooled to room temperature. Fresh sodium methoxide powder was added to "pH 10". The mixture was stirred at room temperature overnight and the clear, orange-yellow reaction mixture was neutralized with Dowex –50 H+ resin, filtered and evaporated in vacuo to yield a pale yellow syrup which slowly crystallized in the freezer overnight. Yield 65 mg, 90%.

Preparation of JO-4B (Formula IV) (Method of E. J. Corey and G. Schmidt, *Tetrahedron Letters*, 399–402, 1979.) JO-4A (50 mg, 0.15 mmol) was dissolved in dichloromethane (I mL) and cooled to 0° C. and 1.5 molar equivalents of pyridinium dichromate was added with efficient stirring. The reaction mixture was allowed to stir at room temperature. for 6 hours and then diluted with ether, filtered and evaporated to yield an off-white solid (30 mg, 60%).

IV

Esters of JO-4

As shown in formula I, the compounds used in the method of the invention comprise esters of JO-4A, including JO-4, which was disclosed in *Heterocycles* 20:212502128 (1983) and in *Z. Naturoorsch* 37c:558–561 (1982).

Accordingly, the method of the invention comprises administering to subjects therapeutically effective amount of at least one hypoestoxide compound having formula I

I in which

R is
H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_n COOR_2$ where n=1–4 where $R_2$ is H, an alkalimetal salt, an alkaline earth metal salt, $NH_4^+$, $N^+(R_3)_4$ where $R_3$ is independently selected from the group consisting of H and alkyl of 1 to 4 carbon atoms, $COR_1$ wherein $R_1$ is selected from the group consisting of H, $(CH_2)_n CH_3$, where n=0–6, $(CH_2)_n COOR_2$ where n=1–4 and $R_2$ is previously defined, $(CH_2)_n N^+(R_3)_4$ wherein n=1–4, and $(CH_2)_n SO_3^-$ where N=1–4, and pharmaceutically acceptable salts thereof.

Preferred embodiments of the invention include pharmaceutical compositions comprising a therapeutically effective amount of the compound of formula II (JO-4A) for inhibiting the growth of cancerous tumors.

Isolation of JO-4 from *Hypoestes rosea*

The general procedure for isolation of pure JO-4 (formula IV) from dried *Hypoestes rosea* plant material involved solid/liquid extraction using boiling hexanes in a large Soxhlet apparatus. *Hypoestes rosea* is a shrub of the family Acantheceac. (Okugun, J. I. et al., Z. Naturforsch 37c:558–561 (1982)) The crude extract obtained from the hexanes upon evaporation was subjected to flash silica gel column chromatography using a step gradient solvent system beginning with petroleum ether (30–60 bp) and stepping to 5% ethyl acetate, then to 10% and then 20%. At 30% ethyl acetate JO-4 was eluted from the column. The appropriate fractions were combined and concentrated to dryness, and petroleum ether or hexanes was added to obtain crystalline JO-4. One such procedure provided 240 mg pure JO-4 from 10 g crude extract from leaves.

Important notes: The crude extract was first dissolved in a minimum of ethyl acetate and absorbed onto silica gel and evaporated to a dry powder before loading onto the column, prepacked in petroleum ether. Extraction of specific parts of the plant indicated that the leaves were the structures that contained the majority of the JO-4 as opposed to the stems.

As shown in the Examples below, the compounds of formula I, and in particular, formula II (JO-4A) were found to have unexpected effectiveness as agents for inhibiting the growth of cancerous tumors as shown by their effects on cancerous tumor cell growth as indicated in standard in vitro and in vivo tests predictive of a compound's anti-tumor activity in vivo in humans or other animals.

The compounds of formula I, in particular formulas II (JO-4A) as demostrated herein, inhibit the growth, formation of, or proliferation or function of cancerous tumor cells, and are therefore useful in a method for inhibiting the growth of cancerous tumors in subjects in need of anticancer treatment.

The effects of the compounds of formula I were determined in the tests described above, the results of which are set forth below. It was found that the medicinal activity of the compounds of formula I for inhibiting the growth of cancerous tumors compounds in the in vitro and mouse in vivo tests formed the basis for the inventors' conclusions that the claimed compounds and the pharmaceutical compositions comprising them have in vivo efficacy in the inhibition of growth of cancerous tumors in an animal or human host.

EXAMPLE 1

Cytotoxic Effects of JO-4A on Cancer Cells in vitro

FIG. 1 is representative of results from several experiments on the cytotoxic effects of JO-4A on various human cancer cells in vitro. The results demonstrated that JO-4A had a dose-dependent cytotoxic effect on human cervical epitheloid carcinoma (HeLa) cells. The inhibitory concentration $_{50}(IC_{50})$, i.e., the drug concentration capable of inducing 50% cytotoxicity, was between 10 $\mu$M and 12.5 $\mu$M.

Similarly, JO-4A had an $IC_{50}$ of between 20 $\mu$M and 40 $\mu$M on renal carcinoma (CAKI-1) cells and between 10 $\mu$M and 12.5 $\mu$M on a malignant melanoma, which metastasizes to lymph node (RPMI-7951).

FIG. 2 shows the cytotoxic effects of JO-4A on normal human cells. When normal human cervical ectoepithelial cells, a control cell line for human cervical epitheloid carcinoma (HeLa) were used in the colorimetric assay, JO-4A had an $IC_{50}$ of >100 μM. The $IC_{50}$ dose for HeLa (between 10 μM and 12.5 μM) had only 6% cytotoxic effect on its normal counterpart. Furthermore, JO-4A had no cytotoxic effect on normal human peripheral blood mononuclear cells. $IC_{50}$ concentration of JO-4A for normal human mammary epithelial cells and normal human umbilical vein endothelial cells were similar (between 25 μM and 50 μM).

Figure 3:
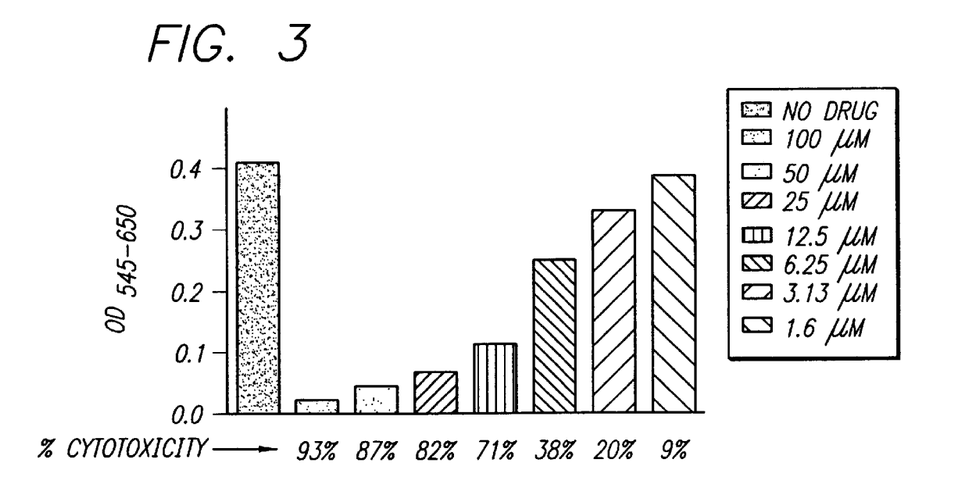
FIG. 3 shows the dose-dependent cytotoxic effect of JO-4A on mouse malignant melanoma (B16-F1) cell line. B16-F1 cells were cultured either in the presence or absence of various concentrations of JO-4A for 72 hours. Cytotoxicity was determined by colorimetric (MTT) assay.

FIG. 3 is representative of results from several experiments on the cytotoxic effects of JO-4A on mouse malignant melanoma cells (B 16-F1) in vitro. The results demonstrated that JO-4A had a dose-dependent cytotoxic effect on B 16-F1 cells. The $IC_{50}$ concentration was between 6.25 μM and 12.5 μM.

EXAMPLE 2

In vivo Effect of JO-4A on Melanoma Tumor Growth

FIG. 4 shows the in vivo effect of JO-4A on B16-F1 melanoma tumor in C57BL/6 (B6) mice. Oral administration of JO-4A daily in B6 mice from day 4 post tumor implantation had significantly reduced tumor volume with all four concentrations of JO-4A tested (FIG. 4A). Furthermore, the oral administration of JO-4A also increased survival of B6 mice in the experimental group. Whereas all the mice (n=6) in the non-treated group were dead by day 28, 84% of the mice (5/6) treated with 2 mg/Kg JO-4A survived. Furthermore, 67% (4/6) of the group treated with 1 mg/Kg, 60% (3/5) of the group treated with 0.5 mg/Kg and 17% (1/6) of the group treated with 0.1 mg/Kg survived (FIG. 4B).

FIG. 5 shows a comparison of survival of each mouse in 2 mg/Kg JO-4A-treated group with non-treated group. The group of mice treated with 2 mg/Kg JO-4A survived longer than the non-treated group, in spite of the fact that treatment was stopped on day 20.

EXAMPLE 3

In vitro Effect of JO-4A in Combination with Interferon-α

Figure 6:
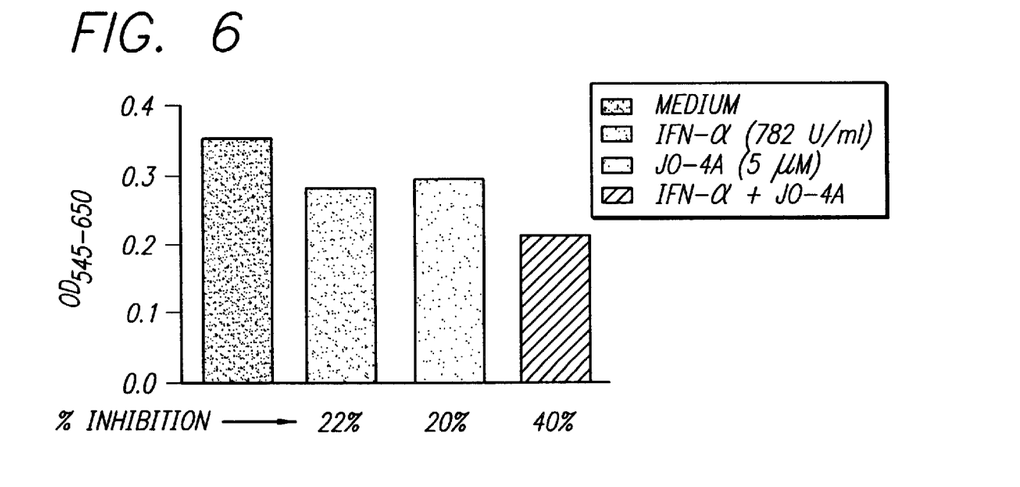
FIG. 6 shows the effect of JO-4A in combination with IFN-alpha on the growth of human malignant melanoma in vitro.

FIG. 6 shows that JO-4A used in combination with interferon-α (IFN-α) produced an additive growth-inhibiting effect on human malignant melanoma in vitro. The results also demonstrated that, in combination with JO-4A, the dose of IFN-α was reduced eight-fold without compromising efficacy of IFN-α. This result finds utilty for patients undergoing IFN-α therapy because high doses of IFN-α are very toxic (*Seminars in Oncology*, Vol. 24, No. 1, Suppl. 4, 1997). Accordingly, the invention includes a method for alleviating the toxicity of IFN-α therapy, the method involving coadministering a sufficient amount of JO-4A in patients receiving IFN-α to enable a lowering of IFN-α dosage, thereby relieving the risk of IFN-α toxicity to the patient.

What is claimed is:

1. A method for inhibiting growth of cancer cells sensitive to the compounds of the formulas which comprises administering to a subject in need of anticancer treatment a pharmaceutical composition comprising a therapeutically effective amount of at least one compound having the formula:

I where
  R is H, $PO_3^=$, alkyl of 1 to 12 carbon atoms substituted or unsubstituted, straight chain or branched, 0 to 6 double bonds, $(CH_2)_n$morpholine where n=1–4, morpholinomethylphenyl, orthoaminophenyl, orthohydroxyphenyl, $(CH_2)_nCOOR_2$ where n=1–4
    where $R_2$ is H, an alkalai metal salt, an alkaline earth metal salt, $NH_4^+$, $N^+(R_3)_4$ where $R_3$ is independently selected from the group consisting of H and alkyl of 1 to 4 carbon atoms,
  $COR_1$ wherein $R_1$ is selected from the group consisting of H, $(CH_2)_nCH_3$, where n=0–6, $(CH_2)_nCOOR_2$ where n=1–4 and $R_2$ is previously defined, $(CH_2)_nN^+(R_3)_4$ wherein n=1–4, and $(CH_2)_nSO_3^-$ where N=1–4,
and pharmaceutically acceptable salts thereof.

2. The method of claim 1 wherein said cancer cells are selected from the group of cancer cells consisting of cervical carcinoma, metastatic melanoma, renal cell carcinoma, testicular embryonal carcinoma, and colonic carcinoma.

3. The method of claim 1 wherein R is H.

* * * * *